US007977079B2

(12) United States Patent
Raines et al.

(10) Patent No.: US 7,977,079 B2
(45) Date of Patent: Jul. 12, 2011

(54) NUCLEIC ACID CONSTRUCTS ENCODING CYTOTOXIC RIBONUCLEASE VARIANTS

(75) Inventors: Ronald T. Raines, Madison, WI (US);
Julie C. Mitchell, Madison, WI (US);
Thomas J. Rutkoski, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 271 days.

(21) Appl. No.: 12/177,229

(22) Filed: Jul. 22, 2008

(65) Prior Publication Data

US 2010/0233809 A1 Sep. 16, 2010

Related U.S. Application Data

(62) Division of application No. 11/454,379, filed on Jun. 16, 2006, now Pat. No. 7,416,875.

(60) Provisional application No. 60/960,970, filed on Jun. 16, 2005.

(51) Int. Cl.
*C12N 15/00* (2006.01)
*C12N 5/10* (2006.01)
*C12N 1/21* (2006.01)
*C07H 21/00* (2006.01)
*C12N 9/16* (2006.01)
*C12P 21/00* (2006.01)

(52) U.S. Cl. .................. 435/196; 435/320.1; 435/252.3; 435/325; 435/69.1; 536/23.2

(58) Field of Classification Search .................. 435/196, 435/320.1, 252.3, 325, 69.1; 530/350; 536/23.2
See application file for complete search history.

(56) References Cited

U.S. PATENT DOCUMENTS

| 5,389,537 | A | 2/1995 | Raines et al. |
|---|---|---|---|
| 5,840,296 | A | 11/1998 | Raines et al. |
| 6,280,991 | B1 | 8/2001 | Raines |
| 7,098,016 | B2 | 8/2006 | Raines et al. |
| 7,416,875 | B2 | 8/2008 | Raines et al. |
| 7,655,757 | B2 | 2/2010 | Raines et al. |
| 2005/0261232 | A1 | 11/2005 | Strong et al. |
| 2006/0292137 | A1 | 12/2006 | Raines et al. |
| 2009/0311784 | A1 | 12/2009 | Raines et al. |

FOREIGN PATENT DOCUMENTS

| AU | 778024 | | 3/2005 |
|---|---|---|---|
| AU | 2002301972 | B2 | 3/2006 |
| CA | 2306442 | | 4/2010 |
| EP | 1896579 | A2 | 3/2008 |
| EP | 1023447 | | 8/2008 |
| EP | 1910541 | B1 | 10/2010 |
| IL | 143036 | | 9/2009 |
| JP | 200817144 | | 5/2008 |
| JP | 2008517102 | A1 | 5/2008 |
| WO | 9919494 | A1 | 4/1999 |
| WO | WO 00/31242 | | 6/2000 |
| WO | 0040608 | A | 7/2000 |
| WO | 2006138458 | A1 | 12/2006 |

OTHER PUBLICATIONS

Kappel et al., Current Opinion in Biotechnology 3:548-553, 1992.*
Mullins et al., Hypertension 22(4):630-633, 1993.*
Cameron, E., Molecular Biotechnology 7:253-265, 1997.*
Mullins et al., J. Clin. Invest. 97(7):1557-1560, 1996.*
Houdebine, L., Journal of Biotechnology 98:145-160, 2002.*
Phillips, A.,J. Pharm. Pharmacology 53:1169-1174, 2001.*
Gardlik et al., Med. Sci. Monit. 11(4):RA110-121, 2005.*
Smyth et al., J. Biol. Chem. 238(1):227-234, 1963.
Carsana, A., et al., "Structure of the bovine pancreatic ribonuclease gene: the unique intervening sequence . . . ," Nucleic Acids Research 16:5491-5502 (1988).
Bosch, M., et al., "A Nuclear Localization Sequence Endows Human Pancreatic Ribonuclease with Cytotoxic Activity," Biochemistry 43:2167-2177 (2004).
Kobe, B., et al., "Mechanism of Ribonuclease Inhibition by Ribonuclease Inhibitor Protein based on the Crystal Structure . . . ," J.Mol. Biol. 264:1028-1043 (1996).
Kumar, K., et al., "Selective abolition of pancreatic RNase binding to its inhibitor protein," PNAS 101:53-58 (2004).
Pous, J., et al., "Three-dimensional Structure of a Human Pancreatic Ribonuclease Variant, a Stem Forward in the Design . . . ," J. Mol. Biol. 303:49-59 (2000).
Leland, P.A., et al., "Ribonuclease A Variants with Potent Cytotoxic Activity," Proc. Natl. Acad. Sci. USA 95:10407-10412 (1998).
Leu, Y-J., et al., "Residues Involved in the catalysis, Base Specificity, and Cytotoxicity of Ribonuclease . . . ," The Journal of Biological Chemistry 278:7300-7309 (2003).
Rajamani, D., et al., "Anchor residues in protein-protein interactions," PNAS 101:11287-11292 (2004).
Rutkoski, T.J., et al., "Disruption of Shape-Complementarity Markers to Create Cytotoxic Variants of Ribonuclease A," J. Mol. Biol. 354:41-54 (2005).
Branden et al., Introduction to Protein Structure, Garland Publishing Inc., New York, p. 247, 1991.
Witkowski et al., Biochemistry 38:11643-11650, 1999.
Seffernick et al., J. Bacteriol. 183(8):2405-2410, 2001.
International Search Report dated Nov. 13, 2006 (International Patent Application No. PCT/US2006/023298; filed on Jun. 16, 2006).
Written Opinion dated Dec. 16, 2007 (International Patent Application No. PCT/US2006/023298; filed on Jun. 16, 2006).
International Preliminary Report on Patentability dated Dec. 17, 2007 (International Patent Application No. PCT/US2006/023298; filed on Jun. 16, 2006).
International Search Report dated Aug. 2, 2007 (International Patent Application No. PCT/US2006/023485; filed on Jun. 16, 2006).
Written Opinion dated Dec. 16, 2007 (International Patent Application No. PCT/US2006/023485; filed on Jun. 16, 2006).

(Continued)

*Primary Examiner* — Delia M Ramirez
(74) *Attorney, Agent, or Firm* — Quarles & Brady LLP; Sara D. Vinarov

(57) ABSTRACT

This invention relates to altered forms of members of the RNase A superfamily. An RNase A can be modified to be cytotoxic by altering its amino acid sequence so that it is not bound easily by the ribonuclease inhibitor while still retaining catalytic properties. While earlier work had identified some modifications to RNase A that would result in cytotoxicity, the use of the FADE algorithm for molecular interaction analysis has led to several other locations that were candidates for modification. Some of those modifications did result in RNase A variants with increase cytotoxicity.

15 Claims, 4 Drawing Sheets

OTHER PUBLICATIONS

International Preliminary Report on Patentability dated Dec. 17, 2007 (International Patent Application No. PCT/US2006/023485; filed on Jun. 16, 2006).
International Search Report dated Nov. 23, 2000 (International Patent Application No. PCT/US19927670; filed on Nov. 22, 1999).
Notice of Allowance dated Apr. 17, 2008 (U.S. Appl. No. 11/454,379, filed Jun. 16, 2006).
Non-Final Rejection dated Aug. 9, 2007 (U.S. Appl. No. 11/454,379, filed Jun. 16, 2006).
Non-Final Rejection dated May 16, 2006 (U.S. Appl. No. 11/454,418, filed Jun. 16, 2006).
Non-Final Rejection dated Sep. 5, 2007 (U.S. Appl. No. 11/454,418, filed Jun. 16, 2006).
Non-Final Rejection dated Mar. 9, 2007 (U.S. Appl. No. 11/454,418, filed Jun. 16, 2006).
Final Rejection dated Oct. 31, 2008 (U.S. Appl. No. 11/454,418, filed Jun. 16, 2006).
Advisory Action dated Jan. 13, 2009 (U.S. Appl. No. 11/454,418, filed Jun. 16, 2006).
Murphy et al., "Sensitivity of monomeric and dimeric forms of bovine seminal ribonuclease to human placental ribonuclease inhibitor", Biochem. J. Mol. Biol. 354:41-54 (2005).
Quintessence/Biosciences webpages on Evade TM Ribonucleases.
Boix E.. et al., "Role of the N Terminus in RNase A Homologues: Differences in Catalytic Activity. Ribonuclease Inhibitor Interaction and Cytotoxicity," J. Mol. Biol. 257:992-1007 (1996).
Gaur, D., et al., "Interaction of Human Pancreatic Ribonuclease with Human Ribonuclease Inhibitor," The Journal of Biological Chemistry 276:24978-24984 (2001).
Kobe B. et al., "A structural basis of the interactions between leucine-rich repeats and protein ligands," Nature 374:183-186 (1995).
Lee, J.E., et at, "Cytotoxicity of Bovine Seminal Ribonuclease: Monomer versus Dimer," Biochemistry 44: 15760-15767 (2005).
Leland, P.A., et al., "Endowing Human Pancreatic Ribonuclease with Toxicity for Cancer Cells," The Journal of Biological Chemistry 276:43095-43102 (2001).
Mitchell, J.C., et at, "Rapid atomic density methods for molecular shape characterization," Journal of Molecular Graphics and Modelling 19:325-330 (2001).
Pous, et al., "Three-dimensional structure of human RNase 1 delta N7 at 1.9 A resolution", Acta Cryst. D57:498-505 (2001).
Shaul, et al., "Exploring the Charge Space of Protein-Protein Association: A Proteomic Study", Proteins: Structure, Function, and Bioinformatics 60:331-352 (2005).
Ontjes et al. (PNAS, Oct. 1969, 64(2):428-35).
Burgess et al. (J. Cell Biol. 111:2129-2138, 1990).
Lazar et al. (Mol. Cell Biol. 8:1247-1252, 1998).
Murthy et al., Sensitivity of monomeric and dimeric forms of bovine seminal ribonuclease to human placental ribonuclease inhibitor (Biochem. J., 1992, 281:343-348).
Gura (Science, 1997, 278:1041-1042).
Non-Final Rejection dated Feb. 9, 2011 (U.S. Appl. No. 12/497,038, filed Jul. 2, 2009).
Requirement for Restriction/Election dated Oct. 5, 2010 (U.S. Appl. No. 12/497,038, filed Jul. 2, 2009).
Communication under Rule 71(3) EPC dated May 4, 2010 (Application No. 06784926.5, filed Jun. 16, 2006).
Examination Report dated Aug. 19, 2009 (EP Patent Application No. 06784995.0-2401, filed Jun. 16, 2006).
Examination Report dated Nov. 2, 2010 (EP Patent Application No. 06784995.0-2401, filed Jun. 16, 2006).
Examination Report dated Nov. 21, 2008 (Application No. 06784926.5, filed Jun. 16, 2006).
Examination Report dated Aug. 25, 2008 (European Patent Application No. 99962862821.7, filed Nov. 22, 1999).
Examination Report dated Jan. 20, 2005 (European Patent Application No. 99962862821.7, filed Nov. 22, 1999).
Notice of Allowance dated Jan. 10, 2004 (Australian Patent Application No. 19184/00; filed Mar. 3, 2005).
Examiner's Report dated Jan. 17, 2003 (Australian Patent Application No. 19184/00; filed Mar. 3, 2005).
Office Action dated Nov. 24, 2009 (Canadian Patent Application No. 2,351,735, filed Nov. 22, 2009).
Office Action dated Nov. 28, 2007 (Canadian Patent Application No. 2,351,735, filed Nov. 22, 2009).
Messmore, et al., Ribonuclease A: Revealing structure—function relationships with semi synthesis, Journal of the American Chemical Society, vol. 117, No. 31, (Aug. 9, 1995).
Reddy, et al, Folate-mediated targeting of therapeutic and imaging agents to cancer, Critical Reviews in Therapeutic Drug Carrier Systems, vol. 15, No. 6, 1998, pp. 587-627.
Kim, et al., Mechanism of ribonuclease cytotoxicity, the Journal of of Biological Chemistry, vol. 270, No. 52 (Dec. 29, 1995) pp. 31097-311102.
Office Action dated Aug. 6, 2009 (Japanese Patent Application No. 2000-584053, filed Nov. 22, 1999).
Final Rejection (Japanese Patent Application No. 2000-584053, filed Nov. 22, 1999).
International Search Report dated Feb. 16, 2009 (International Patent Application No. PCT/US1998/021545, filed Oct. 13, 1998).
Sendak, et al., Kinetic and thermodynamic studies of the folding/unfolding of a tryprtophan-containing mutant of rubinuclease A, Biochemistry, col. 35, 1996, pp. 12978-12992.
Schultz et al., Structure stability of the P93G variant of ribonuclease A, Protein Science, vol. 7, Jul. 1998, pp. 1620-1625.
Communication under Rule 71(3) EPC (European Patent Application No. 98951054.0-2401, filed Oct. 13, 1998).
Examination Report dated May 14, 2003 (European Patent Application No. 98951054.0-2401, filed Oct. 13, 1998).
Examination Report dated Mar. 9, 2004 (European Patent Application No. 98951054.0-2401, filed Oct. 13, 1998).
Examination Report dated Apr. 27, 2005 (European Patent Application No. 98951054.0-2401, filed Oct. 13, 1998).
Notice of Allowance dated Sep. 29, 2009 (Canadian Patent Application No. 2306442, filed Oct. 13, 1998).
Office Action dated Dec. 4, 2007 (Canadian Patent Application No. 2306442, filed Oct. 13, 1998).
Office Action dated Oct. 20, 2006 (Canadian Patent Application No. 2306442, filed Oct. 13, 1998).
Examiner's Report dated Nov. 17, 2004 (Australian Patent Application No. 2002301972, filed Nov. 13, 2006).
Examiner's Report dated Aug. 10, 2005 (Australian Patent Application No. 2002301972, filed Nov. 13, 2006).
Notice of Acceptance dated Nov. 22, 2005 (Australian Patent Application No. 2002301972, filed Nov. 13, 2006).
Kim et al., Structural Basis for the Biological Activities of Bovine Seminal Ribonuclease, J. Biol. Chem. 270, No. 18:10525-10530, 1995.
Schein, From Housekeeper to Microsurgeon: The Diagnostic and Therapeutic Potential of Ribonucleases, Nature Biotechnology 15:529-536, 1997.
Alfacell Corporaton, Reports and Press Releases from Oct. 1994-Nov. 1996.

* cited by examiner (a)

(b)

SEQUENCE LISTING

```
<160> NUMBER OF SEQ ID NOS: 1

<210> SEQ ID NO 1
<211> LENGTH: 124
<212> TYPE: PRT
<213> ORGANISM: Bos taurus

<400> SEQUENCE: 1

Lys Glu Thr Ala Ala Ala Lys Phe Glu Arg Gln His Met Asp Ser Ser
1               5                   10                  15
```

-continued

```
Thr Ser Ala Ala Ser Ser Ser Asn Tyr Cys Asn Gln Met Met Lys Ser
            20              25              30

Arg Asn Leu Thr Lys Asp Arg Cys Lys Pro Val Asn Thr Phe Val His
        35              40              45

Glu Ser Leu Ala Asp Val Gln Ala Val Cys Ser Gln Lys Asn Val Ala
    50              55              60

Cys Lys Asn Gly Gln Thr Asn Cys Tyr Gln Ser Tyr Ser Thr Met Ser
65              70              75              80

Ile Thr Asp Cys Arg Glu Thr Gly Ser Ser Lys Tyr Pro Asn Cys Ala
            85              90              95

Tyr Lys Thr Thr Gln Ala Asn Lys His Ile Ile Val Ala Cys Glu Gly
            100             105             110

Asn Pro Tyr Val Pro Val His Phe Asp Ala Ser Val
        115             120
```

NUCLEIC ACID CONSTRUCTS ENCODING CYTOTOXIC RIBONUCLEASE VARIANTS

CROSS-REFERENCE TO RELATED APPLICATIONS

This application is a divisional of U.S. application Ser. No. 11/454,379, filed Jun. 16, 2006, and issued as U.S. Pat. No. 7,416,875, which claims priority from U.S. provisional patent application Ser. No. 60/690,970 filed Jun. 16, 2005. Each of these applications is incorporated herein by reference in its entirety.

STATEMENT REGARDING FEDERALLY SPONSORED RESEARCH OR DEVELOPMENT

This invention was made with United States government support awarded by the following agency: NIH CA073808. The United States government has certain rights in this invention.

BACKGROUND OF THE INVENTION

Ribonucleases are enzymes that catalyze the degradation of RNA. A well studied ribonuclease is bovine ribonuclease A (RNase A), the putative biological function of which it to break down the large amount of RNA that accumulates in the ruminant gut. The RNase A superfamily is a group of ribonuclease enzymes classified as homologous to RNase A. Some of the members of the superfamily possess a number of interesting biological properties including antiproliferative, cytotoxic, embryotoxic, aspermatogenic, and antitumoral activities. One member of this family is a homolog of RNase A originally isolated from oocytes and early embryos of the Northern leopard frog *Rana pipiens*, which is now known as Onconase® (ONC), a name used for the molecule which exhibits anti-tumor properties both in vitro and in vivo. The property of degrading RNA is essential to the cytotoxicity of ONC. ONC is currently being evaluated as a cancer therapeutic in clinical trials.

A significant limitation on the suitability of ONC as a chemotherapeutic is dose-limiting renal toxicity. ONC is retained in the kidney at concentrations much greater than mammalian members of the RNase superfamily. There may also be allergenic issues with ONC, since mice produce antibodies against ONC but not against RNase A, with which ONC shares about 30% of its amino acids. This suggests that other members of the RNase family may also be suitable candidates for evaluation as clinical therapeutics if they can be imbued with the cytotoxic properties similar to ONC.

In the body, levels of RNase activity are controlled by a ribonuclease inhibitor (RI), which is a 50-kDa protein found in the cytosol of all mammalian cells. RI is a member of a leucine rich family of proteins and is composed of 15 alternating repeats arranged symmetrically in a horseshoe-shaped molecule. RI has a large number of cysteine residues (32 in human RI) which means that it can only keep its shape and function in a reducing environment like the cytosol. RI acts to bind to members of the RNase superfamily, one RI to one molecule of RNase, and when so bound, RI completely inhibits the catalytic activity of the ribonuclease by steric blockage of the active site of the enzyme. The binding of RI to RNase is a very tight one, having a very high binding affinity.

Some RNase superfamily members, notably ONC and bovine seminal ribonuclease, possess the native ability to evade RI. The trait of evasion of RI is primarily responsible for the cytotoxicity of ONC and bovine seminal ribonuclease.

It has also been found that RNase superfamily members which are not natively cytotoxic can be made cytotoxic by modifying their amino acid constituents so as to inhibit binding to RI, and in particular, by making substitutions of larger amino acids for smaller ones at one of the points of closest interaction between RI and the RNase. This method is described in U.S. Pat. No. 5,840,296, which describes a cytotoxic variant, G88R RNase A, which has lessened affinity for RI compared to native RNase A, but which is still ten fold less cytotoxic than ONC. The nomenclature G88R means that the RNase A molecule was altered by substituting an arginine (R) residue for the glycine (G) residue at amino acid position 88.

The methods and tools for modeling the three-dimensional structure of proteins continue to evolve. In analyzing the interaction between two molecules, such as that between RNase A and RI, the problem of defining the sites of interaction between the two molecules is only now becoming susceptible to solution. As molecular modeling tools develop, the sophistication of the analysis of that interaction can increase.

BRIEF SUMMARY OF THE INVENTION

The present invention is summarized by an engineered ribonuclease of the RNase A superfamily having at least two amino acid changes from its native sequence. The first change is an amino acid substitution in the region corresponding to amino acid residues 85 to 94 of bovine pancreatic RNase A (SEQ ID NO: 1). The second change is an alteration, substitution or amino acid swap at a location selected from the groups consisting of an amino acid corresponding to residues 38, 39, and 67 of bovine pancreatic RNase A.

It is an object of the present invention to define an engineered ribonuclease A that has improved cytotoxic properties compared to the prior engineered ribonucleases.

Other objects, advantages and features of the present invention will become apparent from the following specification taken in conjunction with the accompanying drawings.

DETAILED DESCRIPTION OF THE INVENTION

Figure 1:
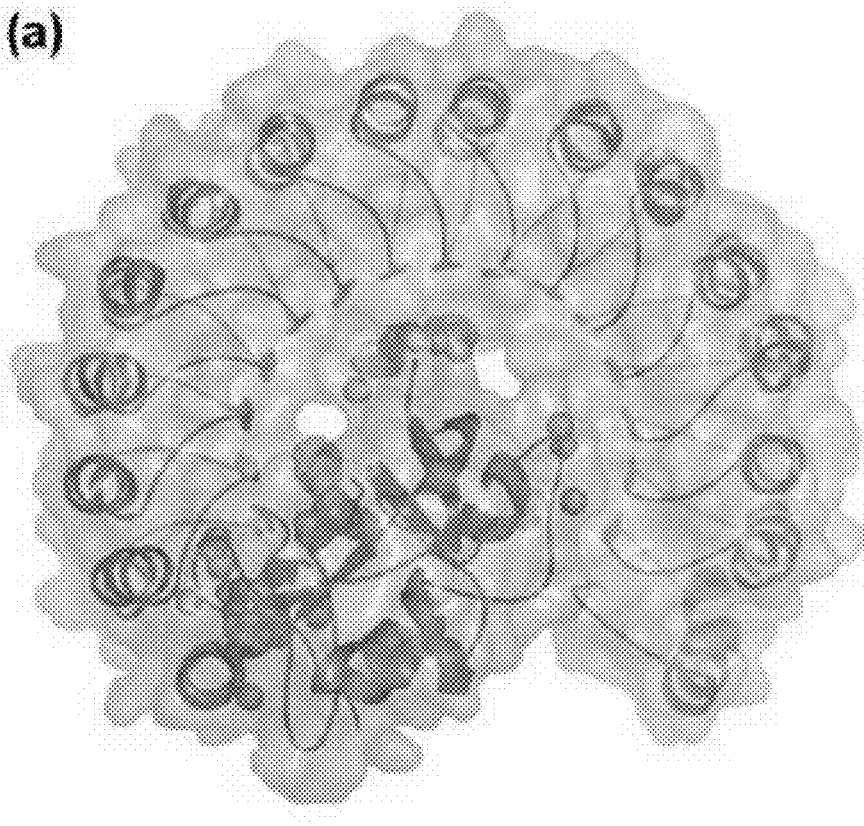
FIG. 1 is a representation of the three-dimensional structure of ribonuclease A and of ribonuclease inhibitor.
Figure 1:
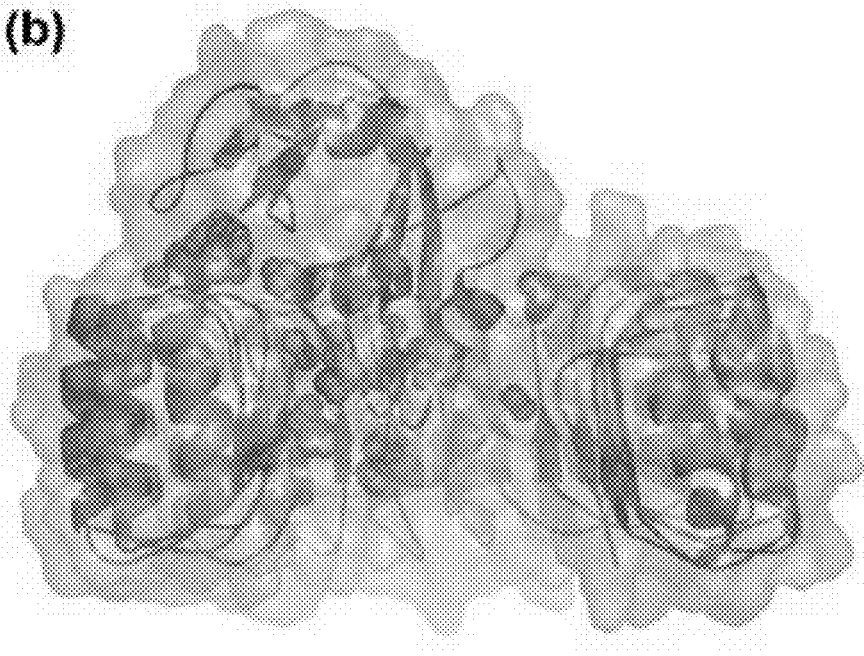

The present invention is directed to altered ribonucleases of the superfamily of RNase A which have been engineered to have a new level of cytotoxicity. This was achieved through the use of a new molecular interaction modeling tool, the Fast Atomic Density Evaluation (FADE) algorithm. This algorithm was used to model the locations of molecular contact between RNase A and the ribonuclease inhibitor. Based on this model, variants in the amino acid sequence of RNase A were designed in order to create novel RNase A variants that through steric hindrance are able to evade the RI. These variants were also tested for ribnucleolytic activity and for cytotoxicity. Variants are identified here that are more cytotoxic than any previously know RNase A variants.

The analysis began with a study of the interaction between RNase A and the RI molecule. There are many properties of a protein-protein interface that can endow the complex with stability, including total surface area, nonpolar surface area, packing density, and polar interactions. The 2,550 Å$^2$ of solvent-accessible surface area buried upon formation of the pRI•RNase A complex is relatively large for an enzyme•inhibitor complex, and is considerably larger than the 1600 Å$^2$ that is typical for protease•inhibitor complexes. In general, protein interfaces resemble the chemical character of solvent-exposed protein surfaces, which are comprised of approximately 57% nonpolar, 24% neutral polar, and 19% charged amino acid residues. Typical protein-protein interfaces do, however, contain fewer charged residues and more neutral polar residues than do solvent-exposed protein surfaces. Deviating from this trend, the pRI-RNase A interface is significantly more charged, with 49% nonpolar, 27% neutral polar, and 24% charged residues. Indeed, electrostatics seem to play an important role in the complex formed between the basic Rnase A (pI 9.3) and the acidic RI protein (pI 4.7) at cytosolic pH.

In contrast to the larger role of charge-charge interactions within the pRI•RNase A complex, the degree of shape complementarity between the two surfaces is lower than average. The shape correlation statistic, $S_c$, describes how well two surfaces mesh, with a value of 1.0 describing a perfect match and 0.0 describing two unrelated surfaces. The pRI•RNase A interface has a relatively low $S_c$ value of 0.58, as compared to values of 0.70-0.76 for typical protease•inhibitor complexes and 0.64-0.68 for typical antibody•antigen complexes. The packing of atoms at the pRI-RNase A interface is also less dense than a typical protein interior or protein-protein interface. The large amount of buried surface area could compensate for the relatively low degree of shape complementarity, to yield a highly stable interaction between RI and RNase A.

Prior to the work described here, K7A/K41R/G88R RNase A was the most RI-evasive of previously produced variants. Again, under the nomenclature used here, G88R means that the RNase A molecule was altered by substituting an arginine (R) residue for the glycine (G) residue at amino acid position 88, and the accumulation of K47A/K41R/G88R means that all three substitutions were made to the same RNAse A variant. This variant formed a complex with pRI that had a $K_d$ value of 47 nM, nearly $10^2$-fold greater than that of G88R RNase A. Still, K7A/K41R/G88R RNase A is not a potent cytotoxin, owing largely to the $10^2$-fold decrease in ribonucleolytic activity caused by the replacement of its active-site lysine residue with arginine. Thus to be effective as a cytotoxic agent, the variant must combine reduced affinity to the RI with the maintenance of effective catalytic activity as an RNAse.

The FADE algorithm revealed new "knobs" and "holes" in the pRI•RNase A complex for disruption by site-directed mutagenesis as illustrated in FIGS. 1 and 2, and listed in Table 1. In the RNase A variants created in this work, the D38R/R39D swap and N67R substitution produced the largest decrease in affinity for RI. Alone, each of these substitutions effected a destabilization of the pRI•RNase A complex nearly equal to that of the G88R substitution. Combining the most disruptive FADE-inspired substitutions resulted in ribonucleases that were not only 30-fold more RI-evasive than K7A/K41R/G88R RNase A, but also retained nearly wild-type catalytic activity (see Table 2 below). Moreover, the D38R/R39D/G88R, D38R/R39D/N67R/G88R, and K31A/D38R/R39D/N67R/G88R variants were all more cytotoxic to K-562 cells than was ONC (see FIG. 3).

The application of the FADE algorithm to the interaction of RNase A and RI thus lead to models of the interaction between the structures of the two molecules as illustrated in FIGS. 1 and 2. This analysis was performed with bovine RNase A and porcine ribonuclease inhibitor (pRI). In these figures, FADE geometric complementarity markers are displayed as solid spheres. These spheres do not represent atoms. Instead, the spheres represent points in the molecular interface near which local complementarity is most significant. Complementarity markers within 2 Å of any atom within a particular residue were summed to determine the cluster sizes listed in Table 1. The residues in RNase A that were proximal to the largest number of complementarity markers and distal from the enzymic active site of RNase A were targeted for disruption.

One interesting finding is the difference in affinity of the porcine and human homologs of RI observed for some of the RNase A variants. In general, the RNase A variants were bound more tightly by pRI than hRI (data presented in Table 2 below). This higher affinity of pRI for RNase A was not observed when the equilibrium dissociation constants were measured originally for complexes of wild-type RNase A with pRI ($K_d$=6.7×$10^{-14}$ M) and hRI ($K_d$=4.4×$10^{-14}$ M). Of the 28 pRI residues that contact RNase A, 25 are identical in hRI. The three differences among the RNase A binding residues are the replacements of His6 in pRI with a glutamine residue in pRI, Asp228 with alanine, and Val405 with leucine. All three of these pRI residues make atom-atom contacts exclusively with FADE-identified RNase A residues. His6 makes three contacts with Lys31 of RNase A, Asp228 makes two contacts with Ser89, and Val405 makes three contacts with Asn67. These three changes are likely to contribute to the differential affinity of pRI and hRI for the RNase A variants.

TABLE 1

Residues of highest shape complementarity in the pRI · RNase A complex as identified with the FADE algorithm

| Chain | Residue | Cluster size[a] |
|---|---|---|
| RNase A | Lys7 | 2 |
| | Asn24 | 5 |
| | Gln28 | 3 |
| | Lys31 | 2 |
| | Arg39 | 31 |
| | Asn67 | 6 |
| | Gly88 | 5 |
| | Ser89 | 14 |
| | Lys91 | 9 |
| RI | Tyr430 | 22 |
| | Asp431 | 10 |
| | Tyr433 | 38 |

[a]Number of FADE complementarity markers within 2 Å of an atom in the indicated residue.

So these residues were the targets for potential modification. Note the variants at the position Gly88 had previously been explored, as described in U.S. Pat. No. 5,840,296, so we looked at other alterations, alone or in combination with G88R. We reasoned that disruption of the RI-RNase A complex could, in general, be achieved best by replacing small neutral or anionic residues in RNase A with arginine. We suspected that arginine, as the most polar and second largest amino acid, could generate electrostatic repulsion and steric strain while increasing the net positive charge, which is known to enhance cell internalization. In addition, we replaced lysine residues in RNase A with alanine to create truncated neutral side chains and thereby eliminate favorable interactions within the complex.

Figure 2:
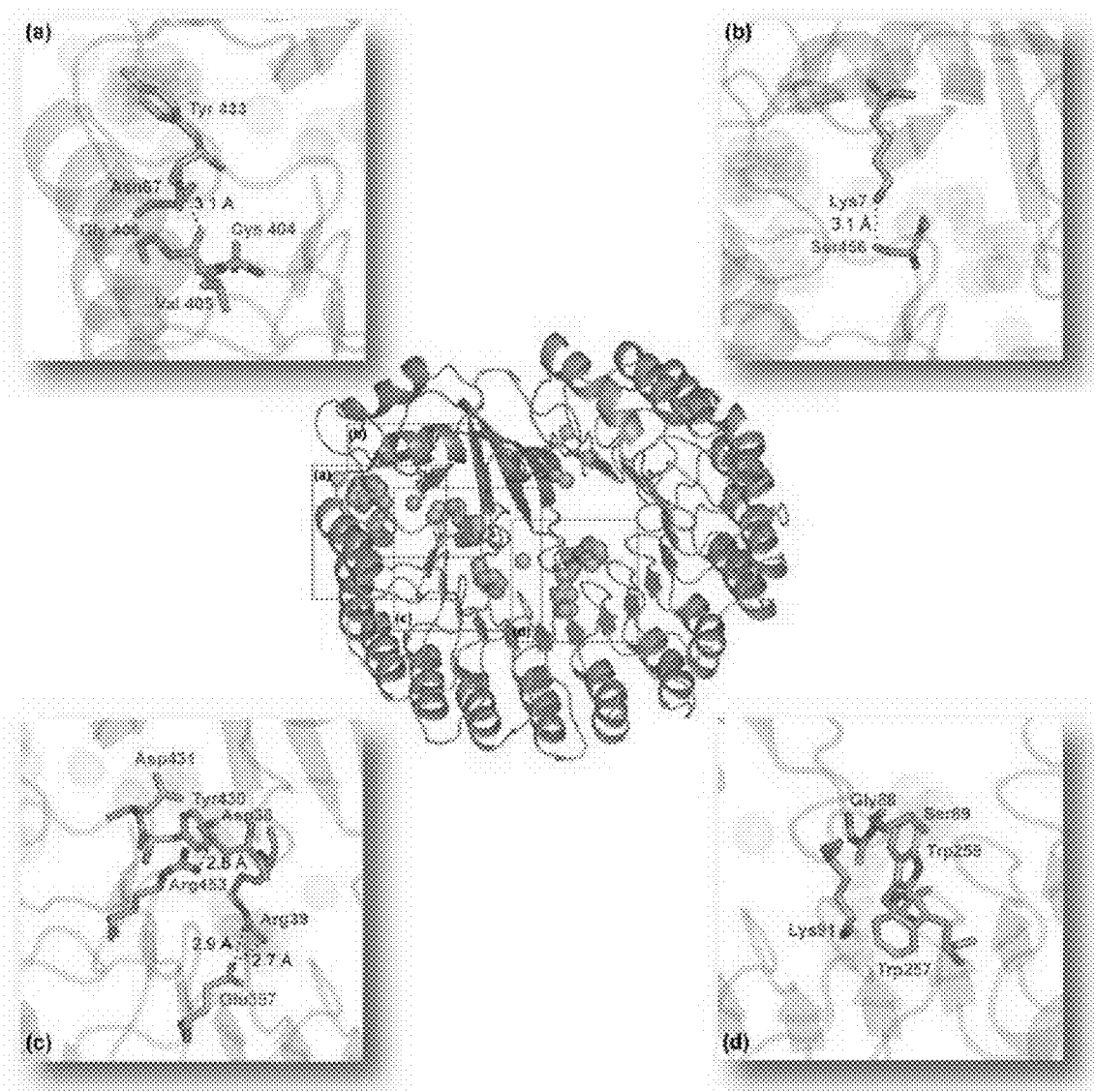
FIG. 2 is a representation of the interaction between the three-dimensional structure of ribonuclease A and ribonuclease inhibitor showing the sites targeted for modifications in the ribonuclease A.
Figure 3:
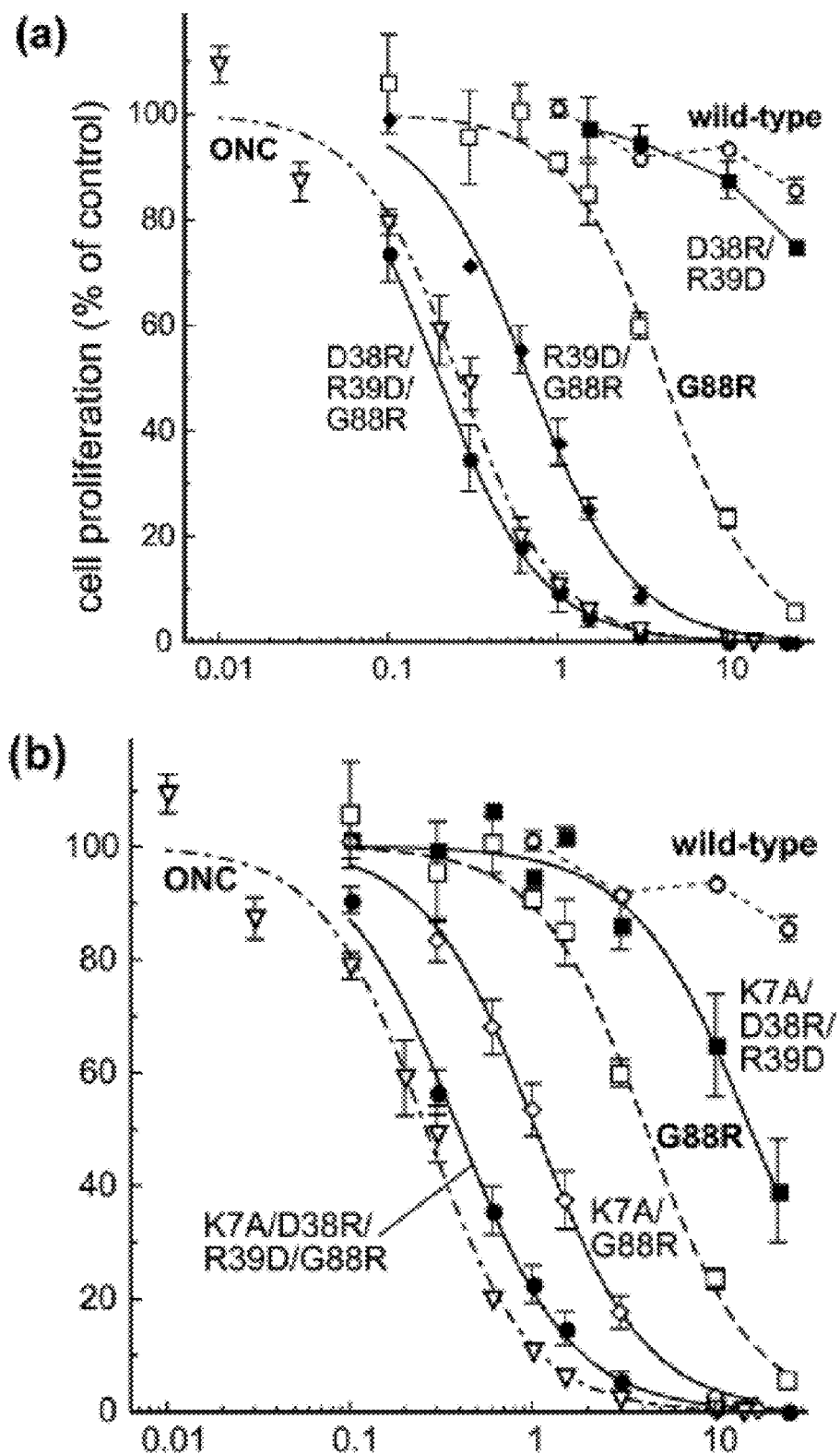
FIG. 3 presents graphical data from the examples below showing the effect of ribonucleases on the proliferation of K-562 cells. The data points are the means of at least three experiments each carried out in triplicate. The curves are each labeled with the corresponding variant of RNase A.
Figure 3:
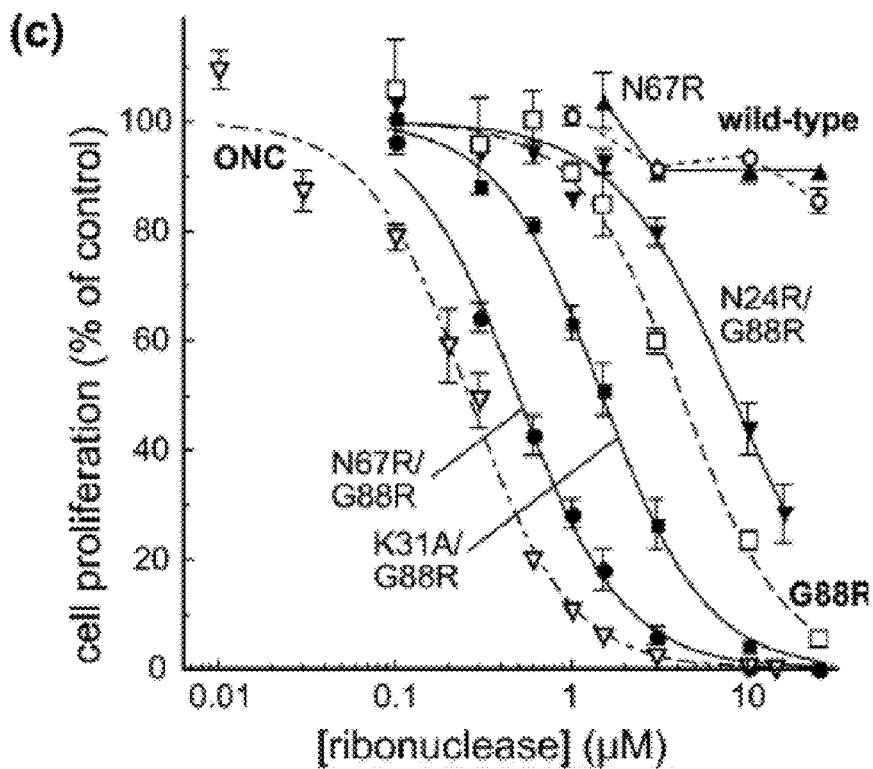
Figure 3:
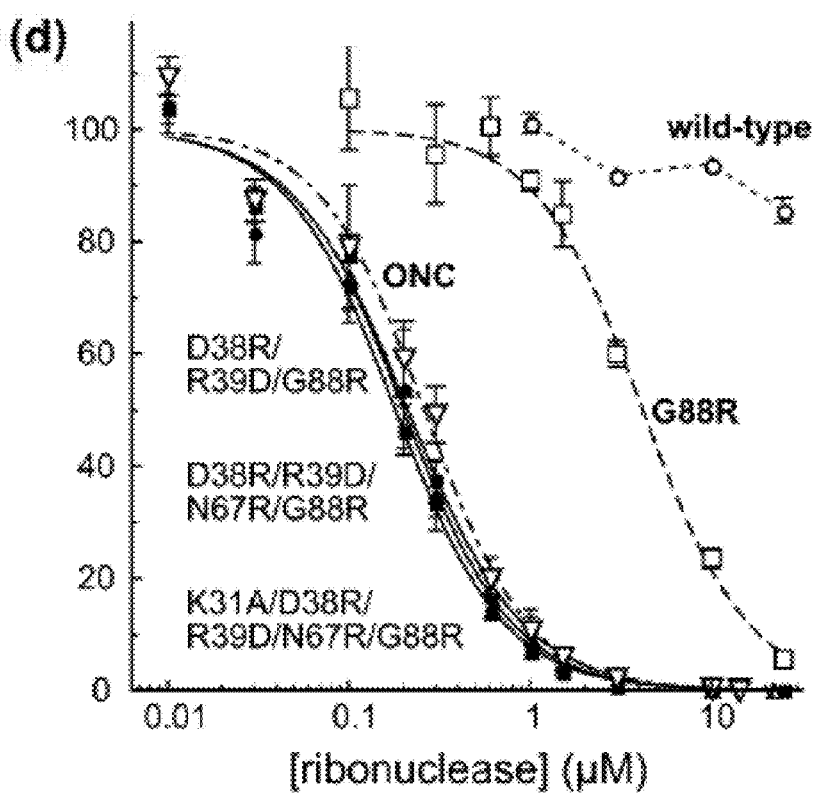

The following substitutions were thus identified as having promise for study:

D38R/R39D Swap (FIG. 2C). Arg39 was identified by the FADE algorithm as being proximal to the greatest number of complementarity markers of any residue in RNase A (Table 1). With 14 atom-atom contacts to pRI, Arg39 also makes more contacts with RI than any residue in RNase A with the exception of Glu111, which also makes 14 contacts. Together, Asp38 and Arg39 of RNase A form three hydrogen bonds with Arg453 and Glu397 of pRI, respectively, with Arg39 interacting with Glu397 in a bidentate manner. Additionally, these two RNase A residues make van der Waals contacts with Gln426, Val428, Tyr430, and Ile455 of RI. Although Asp38 was not identified explicitly by the FADE analysis, we reasoned that by interchanging this residue with Arg39, we could disrupt three favorable interactions at the pRI•RNase A interface simultaneously. Moreover, the D38R/R39D swap was conservative in that it preserved the local amino acid content.

B4-β5 loop (FIG. 2D). Four surface loops of RNase A contribute 16 of the 24 residues that contact RI. The β4-β5 loop of RNase A, containing residues 87-96, packs against an especially hydrophobic region of pRI defined by three tryptophan residues: Trp257, Trp259, and Trp314. Three RNase A residues within this loop, Gly88, Ser89, and Lys91, were identified by FADE as being important for mediating shape complementarity with RI. Earlier attempts to create an RI-evasive RNase A showed the replacement of Gly88 (FADE cluster size 5) with an arginine residue to be extremely effective at introducing steric and electrostatic strain, increasing the $K_d$ value of the pRI•RNase A complex by nearly four orders of magnitude. Therefore, although residues Ser89 and Lys91 were identified by the FADE algorithm as being near large complementarity clusters, we assumed this region of the complex to be disrupted maximally by the G88R substitution and hence did not pursue further alteration of this loop.

N67R substitution (FIG. 2A). Asn67 was proximal to the third largest cluster of complementarity markers, following Arg39 and residues of the β4-β5 loop of RNase A. Asn67 makes six contacts with pRI residues Cys404, Val405, Gly406, and Tyr433, including a hydrogen bond with the main-chain oxygen of Val405. It is noteworthy that Tyr433 of pRI, which makes contacts with Asn67 of RNase A, was identified as being proximal to the largest number of complementarity markers of any residue in either protein. In accordance, Tyr433 of RI and Asn67 of RNase A have been identified by others as the “anchor residues” in the pRI•RNase A complex.

Other FADE-identified residues. Lys7 (FIG. 2B) was the lowest scoring of the RNase A residues with a complementarity cluster size of 2. Nonetheless, Lys7 makes seven atom-atom contacts with Ser456 of pRI, including several hydrogen bonds. Previous studies had shown this residue to contribute significantly to complex stability. We also examined Asn24 and Lys31, which make seven and four atom-atom contacts and are located near cluster sizes of 5 and 2, respectively. Asn24 makes seven van der Waals contacts and two hydrogen bonds with Asp89 and Asp117 of RI; Lys31 makes three atom-atom contacts with His6 of pRI and one contact with Asp31.

While these particular amino acid locations are identified with reference to the specific sequence of bovine pancreatic ribonuclease A, it is to be understood that there are many members of the RNase A superfamily of enzymes to which this information can be applied. Those of skill in the art today understand how to perform sequence alignment and determine for members of this superfamily how to identify the corresponding amino acid location in other members of this closely linked family of enzymes.

To be successful for the purposes we envisioned, the RNase A variants had to have reduced affinity for RI and still retain significant catalytic activity. Hopefully, the combination of reduced affinity for RI and catalytic activity would make the variants cytotoxic and perhaps more cytotoxic than the previous G88R RNase A variants. So modifications of the enzyme at each of the locations identified above were tried and the results presented in the Examples below. This work established that several of these variants exhibited increased cytotoxicity. In particular, the variants D38R/R39D/G88R and D38R/R39D/N67R/G88R both exhibited lowered affinity for RI, a high level of catalytic activity and both were found to have increased cytotoxicity, as exemplified by the data presented in Tables 2 and 3 below.

We used the FADE algorithm to identify quickly and objectively RNase A residues within the pRI•RNase A complex that exhibit a high degree of shape complementarity. Several of the residues identified by the FADE algorithm were previously shown experimentally to contribute a significant amount of binding energy to the pRI•RNase A complex or to be excellent targets for disruption by mutagenesis. The success of the FADE algorithm in predicting the importance of these regions gave credence to its utility and justified our subsequent analysis of additional RNase A residues identified by FADE. Although, a similar list of residues could have been identified by careful examination of the three-dimensional structure, the evident advantage of FADE is the extreme speed at which it identifies regions of high complementarity. Additionally, the computational algorithm is objective, eliminating possible human error or bias.

An important characteristic of any drug is its therapeutic index, which is the ratio of its toxic dose to its effective dose. In humans, ONC exhibits a highly favorable therapeutic index as a cancer chemotherapeutic, enabling its progress to Phase III clinical trials. Mammalian ribonucleases could exhibit an even greater therapeutic index than does ONC. For example, the Hep-3B liver carcinoma cell line is the most vulnerable to all of the ribonucleases tested herein (Table 3). ONC has a therapeutic index (TI), here defined as $IC_{50}^{NmuMG}/IC_{50}^{Hep\text{-}3B}$, of 31. In contrast, the D38R/R39D/N67R/G88R, D38R/R39D/G88R, and G88R variants of RNase A have TI values of >323, >500, and >118, respectively. A biochemical explanation for the therapeutic index of ribonucleases (amphibian or mammalian) awaits further experimentation.

Examples

Experimental Protocol and Results

To explore which of the potential RNase A variants would be successful, we make expression vectors and produced each RNase A variants for each of the propose alterations suggested above. Those variants were than tested for their catalytic properties, their affinity for RI, their stability and their cytotoxicity.

Catalytic Activity

A ribonuclease must retain its catalytic activity to be cytotoxic. Accordingly, the catalytic activity of each ribonuclease was assayed to determine which, if any, of the amino acid substitutions compromised cytotoxicity by reducing the ability of the enzyme to degrade RNA. Values of $k_{cat}/K_M$ for wild-type RNase A, its variants, and ONC are listed in Table 2, which summarizes the results of this analysis. The $k_{cat}/K_M$ values of wild-type RNase A, G88R RNase A, K7A/G88R RNase A, and ONC were $5.2 \times 10^7$, $7.4 \times 10^7$, $5.3 \times 10^6$, and $2.2 \times 10^5$ $M^{-1}s^{-1}$, respectively, which are in good agreement with values reported previously. Swapping residues 38 and 39 of RNase A had a minor effect on catalysis by the enzyme. The value of $k_{cat}/K_M$ for D38R/R39D RNase A was $1.8 \times 10^7$ $M^{-1}s^{-1}$, which represents only a 3-fold loss in ribonucleolytic activity. A similarly small effect was seen in the D38R/R39D/G88R variant; its $k_{cat}/K_M$ value of $3.1 \times 10^7$ $M^{-1}s^{-1}$ was 2.5-fold less than that of G88R RNase A. Interestingly, when the single R39D substitution was made in the context of the G88R substitution, the effect on ribonucleolytic activity was more pronounced, reducing the $k_{cat}/K_M$ value of G88R RNase A by 17-fold to $4.3 \times 10^6$ $M^{-1}s^{-1}$. This decrease could result from enhanced negative charge in this region, possibly reducing the number of productive collisions between the enzyme and its anionic substrate.

The P2 substrate binding site of RNase A, which contains Lys7, plays an important role in catalysis by RNase A. Consistent with previous results, K7A/G88R RNase A displayed an almost 10-fold decrease in ribonucleolytic activity, having a $k_{cat}/K_M$ value of $5.3 \times 10^6$ $M^{-1}s^{-1}$. This deleterious contribution to catalysis was additive when combined with other amino acid substitutions that diminished activity; the D38R/R39D swap (3-fold decrease in $k_{cat}/K_M$) when combined with the K7A substitution (10-fold decrease in $k_{cat}/K_M$) resulted in a K7A/D38R/R39D variant with an activity of $1.6 \times 10^6$ $M^{-1}s^{-1}$, which is 30-fold less than that of wild-type RNase A. Additionally, the K7A substitution was responsible for a 15-fold reduction in the activity of D38R/R39D/G88R RNase A, reducing the activity of the quadruple variant K7A/D38R/R39D/G88R RNase A to $1.6 \times 10^6$ $M^{-1}s^{-1}$.

The majority of the FADE-inspired substitutions had no significant effect on ribonucleolytic activity. The N67R, K31A, and N24R substitutions, when combined individually with the G88R substitution, produced enzymes with catalytic activity roughly comparable to that of G88R RNase A itself. Values of $k_{cat}/K_M$ for these three variants were $9.2 \times 10^7$, $5.2 \times 10^7$, and $7.8 \times 10^7$ $M^{-1}s^{-1}$, respectively. Therefore, RNase A variants combining many of these substitutions (such as K31A/D38R/R39D/N67R/G88R RNase A and D38R/R39D/N67R/G88R RNase A) possessed nearly the $k_{cat}/K_M$ value of the wild-type enzyme ($4.8 \times 10^7$ and $3.8 \times 10^7$ $M^{-1}s^{-1}$, respectively). In short, enzymatic activity did not seem to be a limiting parameter for these variants.

TABLE 2

Biochemical parameters and cytotoxic activities of RNase A, its variants, and ONC

| Ribonuclease | $T_m{}^a$ (°C.) | $k_{cat}/K_M{}^b$ ($10^6 M^{-1}s^{-1}$) | $K_d$ (pRI)$^c$ (nM) | $\Delta\Delta G^d$ (pRI) (kcal/mol) | $K_d{}^e$ (hRI) (nM) |
|---|---|---|---|---|---|
| wild-type Rnase A | 64 | 52 ± 4 | $67 \times 10^{-6h}$ | — | ND |
| D38R/R39D RNase A | 60 | 18 ± 3 | 0.30 ± 0.01 | 5.0 | — |
| N67R RNase A | 57 | 73 ± 19 | 0.36 ± 0.01 | 5.1 | ND |
| K7A/D38R/R39D Rnase A | 62 | 1.6 ± 0.1 | 3.5 | 6.4 | ND |
| N24R/G88R RNase A | 60 | 78 ± 5 | 0.27 | 4.9 | ND |
| G88R RNase A | $60^i$ | 74 ± 4 | $0.57 \pm 0.05^j$ | 5.3 | $7.8^k$ |
| K31A/G88R RNase A | ND | 52 ± 2 | ND | ND | 58 ± 6 |
| K7A/G88R Rnase A | $62^l$ | 5.3 ± 0.4 | 17 ± 1 | 7.4 | 510 ± 20 |
| R39D/G88R RNase A | 61 | 4.3 ± 1 | ND | ND | $(6.4 \pm 0.3) \times 10^3$ |
| N67R/G88R RNase A | 58 | 92 ± 4 | 45 ± 2 | 8.0 | 44 ± 7 |
| K7A/D38R/R39D/G88R RNase A | 60 | 1.6 ± 0.2 | 120 ± 10 | 8.5 | $(27 \pm 3) \times 10^3$ |
| ONC | $90^m$ | 0.22 ± 0.01 | $\geq 10^3$ | — | $\geq 10^3$ |
| D38R/R39D/G88R RNase A | 60 | 31 ± 3 | 8.0 ± 0.4 | 6.9 | 670 ± 40 |
| K31A/D38R/R39D/N67R/G88R RNase A | 54 | 48 ± 7 | ND | — | $(19 \pm 1) \times 10^3$ |
| D38R/R39D/N67R/G88R RNase A | 56 | 38 ± 6 | $(1.4 \pm 0.1) \times 10^3$ | 10.0 | $(3.4 \pm 0.1) \times 10^3$ |

ND, not determined.
$^a$Values of $T_m$ (±2° C.) for RNase A and its variants were determined in PBS by UV spectroscopy.
$^b$Values of $k_{cat}/K_M$ (±SE) for RNase A and its variants are for catalysis of 6-FAM-dArU(dA)$_2$-6-TAMRA cleavage at (23 ± 2)° C. in 0.10 M MES-NaOH buffer (OVS-free) at pH 6.0, containing NaCl (0.10 M). The value of $k_{cat}/K_M$ (±SE) for ONC is for catalysis of 6-FAM-dArUdGdA-6-TAMRA cleavage at (23 ± 2)° C. in 0.020 M MES-NaOH buffer (OVS-free) at pH 6.0, containing NaCl (0.010 M).
$^c$Values of $K_d$ (±SE) are for the complex with pRI at (23 ± 2)° C. The $K_d$ value for ONC is an estimate from Wu et al., (1993) J. Biol Chem. 268, 10686-10693.
$^d$Values of $\Delta\Delta G$ were calculated with the equation: $\Delta\Delta G = -RT\ln(K_d^{wild-type}/K_d^{variant})$.
$^e$Values of $K_d$ (±SE) are for the complex with hRI at (23 ± 2)° C.
$^f$Values of $(k_{cat}/K_M)_{cyto}$ were calculated with eq 1 and values of $K_d$ for the complex with hRI.
$^g$Values of IC$_{50}$ (±SE) are for incorporation of [methyl-$^3$H]thymidine into the DNA of K-562 cells exposed to a ribonuclease, and were calculated with eq 3.
$^h$From Vicentini et al., (1990) Biochemistry 29, 8827-8834.
$^i$From Leland et al., (1998) Proc. Natl. Acad. Sci. USA 95, 10407-10412.
$^j$From Abel et al., (2002) Anal. Biochem. 306, 100-107.
$^k$For fluorescein-labeled G88R RNase A.
$^l$From Haigis et al., (2002) J Biol Chem 211, 11576-11581.
$^m$From Leland et al., (1998) Proc. Natl. Acad. Sci. USA 95, 10407-10412 and determined by circular dichroism spectroscopy.

Affinity for Ribonuclease Inhibitor

The amino acid sequences of pRI and hRI are quite similar (77% identity). Moreover, of the 28 residues in pRI that contact RNase A, only two are replaced by dissimilar residues in hRI. Despite the assumption that the two inhibitor proteins would possess similar affinities for the RNase A variants, we determined the $K_d$ values of complexes with both pRI and hRI. These $K_d$ values are listed in Table 2 above.

As a rigorous test of the utility of the FADE algorithm for identifying residues important for protein-protein interactions, we determined the $K_d$ values of the FADE-inspired variants in complexes with pRI. The $K_d$ values of 0.57 and 17 nM obtained for G88R RNase A and K7A/G88R RNase A in complexes with pRI, were in good agreement with those determined previously. The N24R substitution was the only change that did not diminish the affinity of pRI for RNase A. Indeed, with a $K_d$ value of 0.27 nM, N24R/G88R RNase A actually appeared to form a slightly tighter complex with pRI than did G88R RNase A. The most significant increases in values of $K_d$ were observed for the D38R/R39D swap and the N67R substitution, whose complexes exhibited $K_d$ values of 0.30 and 0.36 nM, respectively. These amino acid changes were responsible for 4,500- and 5,400-fold increases in $K_d$ value, respectively. The K7A/D38R/R39D, N67R/G88R, and D38R/R39D/G88R variants formed complexes with pRI that have $K_d$ values of 3.5, 45, and 8.0 nM, respectively.

The combination of multiple substitutions produced the most RI-evasive variants of RNase A. Of note are the K7A/D38R/R39D/G88R and D38R/R39D/N67R/G88R variants, which formed complexes with pRI having $K_d$ values of 0.12 and 1.4 μM, respectively. Notably, D38R/R39D/N67R/G88R RNase A is the first RNase A variant observed to form a complex with pRI that has a micromolar $K_d$ value. By changing only four out of 124 residues in RNase A, the $K_d$ value of the pRI•RNase A complex was increased by 20-million fold with the D38R/R39D/N67R/G88R variant.

Values of $K_d$ for the complexes of pRI with RNase A variants are ideal for assessing the ability of the FADE algorithm to identify shape-complementarity markers. As a chemotherapeutic, however, cytotoxic ribonucleases must be capable of eluding human RI. For this reason, values of $K_d$ were also determined for the hRI complexes with RNase A variants. With the exception of N67R/G88R RNase A ($K_d$=44 nM), $K_d$ values for the hRI complexes were greater than those obtained for pRI, with the magnitude of the differences ranged from 2- to 230-fold. The highest $K_d$ value observed for a complex with hRI was that of K7A/D38R/R39D/G88R RNase A at 27 μM, which represents a 400 million-fold decrease in affinity for hRI.

Importantly, the destabilizing effects of these substitutions on the complex were not entirely additive, indicating that the pRI•RNase A interface is plastic. The accommodating nature of the binding interface can be seen upon comparison of ΔΔG values (Table 2). For example, the G88R and N67R substitutions destabilized the complex by approximately 5 kcal/mol each. Yet, the N67R/G88R double variant exhibited an 8 kcal/mol loss in binding free energy, despite the spatial separation of these two substitutions.

Stability

The conformational stability of a ribonuclease is necessary for biological function, including cytotoxicity. Hence, the $T_m$ value of each RNase A variant was determined and is listed in Table 2. The N67R substitution was the most destabilizing, decreasing the $T_m$ value of wild-type RNase A by 7° C. to a value of 57° C. This loss in conformational stability was not recovered by additional substitutions, being observed in all variants containing the N67R substitution. The N67R/G88R and D38R/R39D/N67R/G88R variants had $T_m$ values of 58 and 56 C, respectively. K31A/D38R/R39D/N67R/G88R RNase A had the lowest $T_m$ value of 54° C., which is nearly 10 C lower than that of the wild-type enzyme. Still, this $T_m$ value is significantly greater than physiological temperature. None of the other amino acid substitutions reduced the $T_m$ value by more than a few degrees C.

Cytotoxicity

The toxicity of each ribonuclease was measured with the K-562 human leukemia cell line. Ribonucleases are listed in order of increasing cytotoxicity in Table 2, using $IC_{50}$ values derived by applying equation 3 (set forth below) to the data in FIG. 3 (h=1.43±0.02 for the 12 cytotoxic ribonucleases). ONC, G88R RNase A, and K7A/G88R RNase A displayed $IC_{50}$ values similar to those reported previously. D38R/R39D RNase A (FIG. 3A) and N67R RNase A (FIG. 3C) exhibited no cytotoxic activity, even at concentrations of 25 μM. The lack of cytotoxicity for the latter two variants is interesting, considering the large increase in cytotoxicity they exhibited in the context of the G88R substitution.

Upon incorporation of the K7A substitution into the D38R/R39D/G88R variant, its affinity for hRI decreased 40-fold, consistent with the loss of favorable interactions between the lysine side chain and C-terminal serine residue of hRI. This larger $K_d$ value was accompanied by a loss in catalytic activity, leading to an $IC_{50}$ value nearly twice that of D38R/R39D/G88R RNase A. Although Asp38 was not identified explicitly by the FADE analysis, its importance in the conservative D38R/R39D swap is apparent when the $IC_{50}$ value of R39D/G88R RNase A ($IC_{50}$=0.69 μM) is compared with that of D38R/R39D/G88R RNase A ($IC_{50}$=0.22 μM).

Two of the most cytotoxic variants of RNase A discovered in this work, D38R/R39D/G88R and D38R/R39D/N67R/G88R, as well as ONC, wild-type RNase A, and G88R RNase A, were screened for cytotoxic activity against ten different cell lines. The resulting $IC_{50}$ values of these ribonucleases are listed in Table 3. All of the cell lines are of human origin except for NmuMG, which is a mouse mammary normal epithelial cell line. With the exception of the Hep3B cell line, all of the human cancer cell lines, like the human leukemia K-562 line, are among the 60 cell lines screened by the National Cancer Institute in search of novel cancer chemotherapeutics.

The cell lines are listed in Table 3 according to increasing doubling times. There did not appear to be any direct correlation between doubling time and sensitivity to the ribonucleases as had been reported previously. In general, the trend of cytotoxicity among the RNase A variants reflected that seen in the K-562 cell line, namely D38R/R39D/N67R/G88R>D38R/R39D/G88R>G88R>wild-type RNase A, with the D38R/R39D/N67R/G88R variant consistently having the lowest $IC_{50}$ value. The HCT-116, A549, and SF268 cell lines were exceptions to this general trend, as all were more sensitive to wild-type RNase A than was G88R RNase A. Others have reported that wild-type human pancreatic ribonuclease (RNase 1) is toxic to some cell lines, just as we found several cell lines susceptible to wild-type RNase A. These three cell lines derive from three different tissue types: colon, lung, and CNS, respectively.

A goal of this work was to identify RNase A variants possessing cytotoxicity equal to or greater than that of ONC. This goal was achieved with the D38R/R39D/N67R/G88R variant in the K-562, Du145, Hep-3B, and SF268 cell lines. In the remaining six cell lines, ONC exhibited 3- to 30-fold greater cytotoxicity than did the RNase A variants. Interestingly, none of the RNase A-derived variants tested in this screen was toxic to the normal cell line NmuMG at the maximum concentrations tested. This discrimination was not observed with ONC, which had an $IC_{50}$ of 1.62 μM for the normal mouse cell line.

TABLE 3

$IC_{50}$ values of RNase A, its variants, and ONC for ten cell lines

| Cell line | Description | Doubling time (h) | $IC_{50}$ (μM)[a] wild-type | DRNG[b] | DRG[b] | G88R | ONC |
|---|---|---|---|---|---|---|---|
| HCT-116 | colon carcinoma | 17.4 | 4.7 | 0.49 | 1.4 | 10.4 | 0.14 |
| NCI-H460 | lung carcinoma | 17.8 | 39 | 0.71 | 0.60 | 11.0 | 0.13 |
| A549 | lung adenocarcinoma | 22.9 | 15.5 | 4.8 | 13.7 | 27.0 | 0.15 |

TABLE 3-continued IC$_{50}$ values of RNase A, its variants, and ONC for ten cell lines

| Cell line | Description | Doubling time (h) | IC$_{50}$ (μM)[a] | | | | |
|---|---|---|---|---|---|---|---|
| | | | wild-type | DRNG[b] | DRG[b] | G88R | ONC |
| MCF-7 | breast adenocarcinoma | 25.4 | 21.7 | 0.27 | 0.42 | 4.4 | 0.086 |
| Du145 | prostate carcinoma | 32.3 | 5.5 | 0.085 | 0.45 | 2.0 | 0.11 |
| SF-268 | CNS glioblastoma | 33.1 | 3.8 | 0.18 | 0.64 | 4.6 | 0.088 |
| NCI/ADR-RES | breast adenocarcinoma | 34.0 | 19 | 1.00 | 2.3 | 5.8 | 0.06 |
| SK-OV-3 | ovary adenocarcinoma | 48.7 | 3.2 | 0.76 | 1.5 | 2.8 | 0.13 |
| Hep-3B | liver carcinoma | ND | 2.8 | 0.031 | 0.040 | 0.34 | 0.051 |
| NmuMG | mammary normal epithelial (mouse) | ND | >40 | >10 | >20 | >40 | 1.6 |

[a]Values of IC$_{50}$ are for the conversion of calcein AM to calcein in cells exposed to a ribonuclease, and were calculated with eq 4.
[b]DRNG and DRG refer to the D38R/R39D/N67R/G88R and D38R/R39D/G88R variants of RNase A, respectively.

Methods and Materials

Materials

*Escherichia coli* BL21(DE3) cells and pET22b(+) and pET27b(+) plasmids were from Novagen (Madison, Wis.). K-562 cells were derived from a continuous human chronic myelogenous leukemia line obtained from the American Type Culture Collection (Manassas, Va.). Cell culture medium and supplements were from Invitrogen (Carlsbad, Calif.). [methyl-$^3$H]Thymidine (6.7 Ci/mmol) was from Perkin Elmer (Boston, Mass.). Enzymes were obtained from Promega (Madison, Wis.) or New England Biolabs (Beverly, Mass.). Ribonuclease substrates 6-FAM-dArUdAdA-6-TAMRA and 6~FAM-dArUdGdA~6-TAMRA were from Integrated DNA Technologies (Coralville, Iowa). All other chemicals used were of commercial reagent grade or better, and were used without further purification.

Terrific Broth (TB) contained (in 1.00 L) tryptone (12 g), yeast extract (24 g), glycerol (4 mL), KH$_2$PO$_4$ (2.31 g), and K$_2$HPO$_4$ (12.54 g). Phosphate-buffered saline (PBS) contained (in 1.00 L) NaCl (8.0 g), KCl (2.0 g), Na$_2$HPO$_4$.7H$_2$O (1.15 g), KH$_2$PO$_4$ (2.0 g), and NaN$_3$ (0.10 g), and had pH 7.4.

Instruments

[methyl-$^3$H]Thymidine incorporation into K-562 genomic DNA was quantitated by scintillation counting using a Microbeta TriLux liquid scintillation and luminescence counter (Perkin Elmer, Wellesley, Mass.). The mass of each protein variants was confirmed by MALDI-TOF mass spectrometry using a Voyager-DE-PRO Biospectrometry Workstation (Applied Biosystems, Foster City, Calif.). Fluorescence measurements were made with a QuantaMaster1 photon-counting fluorometer equipped with sample stirring (Photon Technology International, South Brunswick, N.J.). Thermal denaturation data were acquired using a Cary 3 double-beam spectrophotometer equipped with a Cary temperature controller (Varian, Palo Alto, Calif.).

Design of Ribonuclease A variants

The Fast Atomic Density Evaluator (FADE) program calculates shape-complementarity markers of proteins at complex interfaces. Atomic density is measured using fast Fourier transform algorithms based on methods described previously. Using the structure of the crystalline pRI•RNase A complex (PDB entry 1DFJ), critical RNase A residues in close proximity to large clusters of shape-complementarity markers were identified and are listed in Table 1 above. Amino acid substitutions were chosen to create maximal electrostatic or steric conflict as well as eliminate any favorable Coulombic or short-range interactions.

At the onset of this research, the most cytotoxic variant of RNase'A known was K7A/G88R RNase A. Subsequent amino acid substitutions inspired by FADE analysis were initially made in the background of these established changes, with the expectation that any additional contributions to evasivity would be additive. As discussed here, we found that the loss of enzymatic activity accompanying the K7A substitution compromised cytotoxicity, and hence, later substitutions were made in the background of the G88R substitution alone. The G88R background provided a well-characterized benchmark of cytotoxicity and RI-evasion from which we could identify improvements using our established assays. Substitutions that were successful in the G88R background were also made alone to assess their individual contribution to evasion of RI and cytotoxicity.

Production of Ribonucleases cDNA molecules encoding RNase A variants were created by oligonucleotide-mediated site-directed mutagenesis using a pET22b(+) or pET27b(+) plasmid that contained cDNA encoding wild-type RNase A or its G88R variant, respectively. ONC, wild-type RNase A, and RNase A variants were produced as described previously in Haigis et al., (2002) *J Biol Chem* 277, 11576-11581, with the following exceptions. Inclusion bodies from *E. coli* were stirred in 20 mM Tris-HCl buffer at pH 8.0, containing guanidine-HCl (7 M), DTT (0.1 M), and EDTA (10 mM) until dissolved thoroughly. Ribonucleases were refolded overnight at room temperature following slow dilution into 0.10 M Tris-HCl buffer at pH 8.0, containing NaCl (0.1 M), reduced glutathione (1.0 mM), and oxidized glutathione (0.2 mM). Following purification, proteins were dialyzed against PBS and filtered with a 0.2 μm syringe prior to use in biochemical assays. Protein concentration was determined by UV spectroscopy using an extinction coefficient of $\epsilon_{278}$=0.72 mg·ml$^{-1}$cm$^{-1}$ for RNase A and its variants and $\epsilon_{280}$=0.87 mg·ml$^{-1}$cm$^{-1}$ for ONC.

Production of Ribonuclease Inhibitor

Porcine ribonuclease inhibitor (pRI) was prepared as described in Klink et al., (2001) *Protein Expr. Purif.* 22, 174-179. Freshly prepared pRI was confirmed to be 100% active by its ability to titrate the ribonucleolytic activity of wild-type RNase A.

Human ribonuclease inhibitor (hRI) was produced in *E. coli* BL21(DE3) cells transformed with a pET22b(+) plasmid that contained cDNA encoding hRI between its NdeI and SalI sites. Cultures (1.0 L) of TB were inoculated to an OD of 0.005 at 600 nm from an overnight culture. The culture was grown at 37 C to an OD of 1.8-2.0 at 600 nm IPTG was added to a final concentration of 0.5 mM, and induction was carried out overnight at 18 C. Subsequent purification of soluble protein and activity determination of hRI was carried out in the same manner as for pRI. The purity and size of both RIs were confirmed by electrophoresis and mass spectrometry.

Assays of Ribonuclease Inhibitor Binding

The affinity of RNase A variants for both pRI and hRI was determined by using a slight modification of a competition assay reported previously in Abel et al., (2002) *Anal. Biochem.* 306, 100-107. Briefly, both fluorescein-labeled G88R RNase A (final concentration: 50 nM) and varying concentrations of an unlabeled ribonuclease were added to 2.0 ml of PBS containing DTT (5 mM). Following a 15 min incubation at (23±2)° C., protected from light, the initial fluorescence intensity of the unbound fluorescein-labeled G88R RNase A was monitored for 3 min (excitation: 493 nm, emission: 515 nm). pRI was then added (final concentration: 50 nM, which is sufficient to bind 90% of the fluorescein-labeled G88R RNase A in the absence of unlabeled competitor), and the final fluorescence intensity was measured. The competition assay was carried out identically for hRI, except that more hRI was necessary (final concentration of 115 nM) to achieve 90% binding of fluorescein-labeled G88R RNase A because of the lower affinity of hRI. The affinity of hRI for fluorescein-labeled G88R RNase A was determined by titrating 50 nM fluorescein-labeled G88R RNase A with varying amounts of hRI (0.5-1000 nM) and recording the decrease in fluorescence upon binding. The value of $K_d$ was found to be 7.8 nM.

Assays of Catalytic Activity

The ribonucleolytic activities of RNase A and its variants were determined by assaying their ability to cleave the hypersensitive fluorogenic substrate 6-FAM~dArUdAdA~6-TAMRA (50 nM), which exhibits a 180-fold increase in fluorescence (excitation: 493 nm, emission: 515 nm) upon cleavage. Assays were carried out at (23±2)° C. in 2.0 ml of 0.10 M MES-NaOH buffer at pH 6.0, containing NaCl (0.10 M). The MES used to prepare the assay buffer was purified by anion-exchange chromatography to remove trace amounts of oligomeric vinylsulfonic acid, which is a byproduct of commercial buffer synthesis and has been shown to be a potent inhibitor of RNase A. Values of $k_{cat}/K_M$ were obtained with the equation:

$$k_{cat}/K_M = \left(\frac{\Delta I/\Delta t}{I_{max} - I_0}\right)\frac{1}{[\text{ribonuclease}]} \quad (1)$$

where $\Delta I/\Delta t$ represents the initial reaction velocity generated by cleavage of the 6-FAM-dArUdAdA-6-TAMRA substrate upon addition of ribonuclease to the cuvette. $I_0$ and $I_{max}$ are, respectively, the fluorescence intensities prior to enzyme addition and following the complete cleavage of substrate by excess wild-type RNase A. Activity values for ONC were determined at (23±2) C in 2.0 ml of OVS-free 20 mM MES-NaOH buffer at pH 6.0, containing NaCl (0.010 M) using the substrate 6-FAM~dArUdGdA~6-TAMRA (50 nM).

Assays of Cytotoxicity $IC_{50}$ values for RNase A, its variants, and ONC were determined by measuring the incorporation of [methyl-$^3$H]thymidine into the cellular DNA of K-562 cells in the presence of ribonucleases. All cytotoxicity assays were repeated at least three times in triplicate. Each data point represents the mean of three or more experimental values (±SE). $IC_{50}$ values were calculated by fitting the curves using nonlinear regression to a sigmoidal dose-response curve with the equation:

$$y = \frac{100\%}{1 + 10^{(\log(IC_{50}) - \log[\text{ribonuclease}])h}} \quad (2)$$

In eq 3, y is the total DNA synthesis following a 4-h [methyl-$^3$H]thymidine pulse, and h is the slope of the curve.

Cytotoxicity assays other than those carried out using K-562 cells were performed at the Keck-UWCCC Small Molecule Screening Facility. These assays used ten cell lines from a broad spectrum of tissues. Following a 72-h incubation with ribonucleases, $IC_{50}$ values were determined by measuring the enzymatic conversion of the profluorophore calcein AM (Molecular Probes, Eugene, Oreg.) to calcein in live cells. Coefficient of variation and Z-scores were determined for each cell line using doxorubicin as an internal control. All cytotoxicity assays were performed in triplicate three times. $IC_{50}$ values were calculated with the equation:

$$IC_{50} = \left(\frac{50\% - \text{low }\%}{\text{high }\% - \text{low }\%}\right)\left(\frac{[\text{ribonuclease}]_{high} -}{[\text{ribonuclease}]_{low}}\right) + [\text{ribonuclease}]_{low} \quad (3)$$

where low % and high % refer to inhibition by the two concentrations, $[\text{ribonuclease}]_{low}$ and $[\text{ribonuclease}]_{high}$, that bracket 50% inhibition.

Although the foregoing invention has been described in some detail by way of illustration and example for purposes of clarity of understanding, it is understood that certain adaptations of the invention are a matter of routine optimization for those skilled in the art, and can be implemented without departing from the spirit of the invention, or the scope of the appended claims.

We claim:

1. A DNA construct encoding an engineered bovine pancreatic ribonuclease A variant, wherein said variant comprises an amino acid sequence which differs from the amino acid sequence of the native bovine ribonuclease A of SEQ ID NO: 1 solely by three or more amino acid substitutions at positions corresponding to positions of SEQ ID NO: 1 selected from the group consisting of 38, 39, 67 and 85-94, wherein at least one of the three or more amino acid substitutions is at a position corresponding to any one of positions 85-94 of SEQ ID NO: 1, wherein at least two of the three or more amino acid substitutions are at positions corresponding to positions 38, 39 or 67 of SEQ ID NO: 1, and wherein the engineered bovine pancreatic ribonuclease A variant exhibits enhanced cytotoxic activity relative to the native bovine ribonuclease A of SEQ ID NO: 1.

2. An isolated host cell comprising the DNA construct of claim 1.

3. A DNA construct encoding an engineered bovine pancreatic ribonuclease A variant differing from the native bovine pancreatic ribonuclease A of SEQ ID NO: 1 at amino acid residue positions 38, 39 and 88 of SEQ ID NO: 1, wherein the difference consists of an aspartic acid at position 38 being changed to an arginine, an arginine at position 39 being changed to an aspartic acid, and a glycine at position 88 being changed to an arginine, 4. A DNA construct encoding an engineered bovine pancreatic ribonuclease A variant differing from the native bovine pancreatic ribonuclease A of SEQ ID NO: 1 at amino acid residue positions 38, 39, 67 and 88 of SEQ ID NO: 1, wherein the difference consists of a aspartic acid at position 38 being changed to an arginine, an arginine at position 39 being changed to an aspartic acid, an asparagine at position 67 being changed to an arginine, and a glycine at position 88 being changed to an arginine.

5. A DNA construct encoding an engineered bovine pancreatic ribonuclease A variant differing from the native bovine pancreatic ribonuclease A of SEQ ID NO: 1 at amino acid residue positions 39 and 88 of SEQ ID NO: 1, wherein the difference consists of an arginine at position 39 being changed to an aspartic acid, and a glycine at position 88 being changed to an arginine.

6. A DNA construct encoding an engineered bovine pancreatic ribonuclease A variant differing from the native bovine pancreatic ribonuclease A of SEQ ID NO: 1 at amino acid residue positions 67 and 88 of SEQ ID NO: 1, wherein the difference consists of an asparagine at position 67 being changed to an arginine, and a glycine at position 88 being changed to an arginine.

7. A DNA construct encoding an engineered bovine pancreatic ribonuclease A variant differing from the native bovine pancreatic ribonuclease A of SEQ ID NO: 1 at amino acid residue positions 39 and 88 of SEQ ID NO: 1, wherein the difference consists of an amino acid substitution at these positions.

8. A DNA construct encoding an engineered bovine pancreatic ribonuclease A variant differing from the native bovine pancreatic ribonuclease A of SEQ ID NO: 1 at amino acid residue positions 67 and 88 of SEQ ID NO: 1, wherein the difference consists of an amino acid substitution at these positions.

9. A DNA construct encoding an engineered bovine pancreatic ribonuclease A variant differing from the native bovine pancreatic ribonuclease A of SEQ ID NO: 1 at amino acid residue positions 38, 39 and 88 of SEQ ID NO: 1, wherein the difference consists of an amino acid substitution at these positions.

10. A DNA construct encoding an engineered bovine pancreatic ribonuclease A variant differing from the native bovine pancreatic ribonuclease A of SEQ ID NO: 1 at amino acid residue positions 38, 39, 67 and 88 of SEQ ID NO: 1, wherein the difference consists of an amino acid substitution at these positions.

11. An isolated host cell comprising the DNA construct of any one of claims 7-10.

12. A DNA construct encoding an engineered bovine pancreatic ribonuclease A variant, wherein said variant comprises an amino acid sequence which differs from the amino acid sequence of the native bovine ribonuclease A of SEQ ID NO: 1 solely by three or more amino acid substitutions at positions corresponding to positions of SEQ ID NO: 1 selected from the group consisting of 38, 39, 67 and 85-94, and wherein the engineered bovine pancreatic ribonuclease A variant has the following biological properties: (i) retains ribonucleolytic activity, and (ii) exhibits enhanced cytotoxic activity relative to the native bovine ribonuclease A of SEQ ID NO: 1.

13. An isolated host cell comprising the DNA construct of claim 12.

14. The DNA construct of claim 1 wherein the engineered bovine pancreatic ribonuclease A variant has the following biological properties: (i) retains ribonucleolytic activity, and (ii) exhibits enhanced cytotoxic activity relative to the native bovine ribonuclease A of SEQ ID NO: 1.

15. A DNA construct encoding an engineered bovine pancreatic ribonuclease A variant, wherein said variant comprises an amino acid sequence which differs from the amino acid sequence of the native bovine ribonuclease A of SEQ ID NO: 1 solely by two or more modifications at positions corresponding to positions of SEQ ID NO: 1 selected from the group consisting of 38, 39, 67 and 85-94, wherein at least one of the two or more modifications is an amino acid substitution at a position corresponding to any one of positions 85-94 of SEQ ID NO: 1, and wherein at least one of the two or more modifications is selected from the group consisting of: (i) a substitution at a position corresponding to position 39 of SEQ ID NO: 1, (ii) a substitution at a position corresponding to position 67 of SEQ ID NO: 1, (iii) substitutions at positions corresponding to positions 38 and 39 of SEQ ID NO: 1, and (iv) substitutions at positions corresponding to positions 38, 39 and 67 of SEQ ID NO: 1.

* * * * *

UNITED STATES PATENT AND TRADEMARK OFFICE
CERTIFICATE OF CORRECTION

PATENT NO.         : 7,977,079 B2                                                      Page 1 of 1
APPLICATION NO.    : 12/177229
DATED              : July 12, 2011
INVENTOR(S)        : Ronald T. Raines, Julie C. Mitchell and Thomas J. Rutkoski It is certified that error appears in the above-identified patent and that said Letters Patent is hereby corrected as shown below:

Column 1, line 16:
Please replace paragraph [0002] under the heading STATEMENT REGARDING FEDERALLY SPONSORED RESEARCH AND DEVELOPMENT: "This invention was made with United States government support awarded by the following agency: NIH CA073808. The United States government has certain rights in this invention."

with:

--This invention was made with government support under CA073808 awarded by the National Institutes of Heath. The government has certain rights to this invention.--

Signed and Sealed this
Eighteenth Day of October, 2011

David J. Kappos
*Director of the United States Patent and Trademark Office*